(12) United States Patent
Pokrovski et al.

(10) Patent No.: US 9,334,207 B2
(45) Date of Patent: May 10, 2016

(54) INTEGRATED PROCESS TO COPRODUCE TRANS-1-CHLORO-3,3,3-TRIFLUOROPROPENE, TRANS-1,3,3,3-TETRAFLUOROPROPENE, AND 1,1,1,3,3-PENTAFLUOROPROPANE

(75) Inventors: Konstantin A. Pokrovski, Orchard Park, NY (US); Daniel C. Merkel, Orchard Park, NY (US); Haiyou Wang, Amherst, NY (US); Hsueh Sung Tung, Getzville, NY (US); Ian Shankland, Randolph, NJ (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 13/219,831

(22) Filed: Aug. 29, 2011

(65) Prior Publication Data

US 2012/0059200 A1    Mar. 8, 2012

Related U.S. Application Data

(60) Provisional application No. 61/379,745, filed on Sep. 3, 2010.

(51) Int. Cl.
*C07C 17/00* (2006.01)
*C07C 17/25* (2006.01)
(Continued)

(52) U.S. Cl.
CPC .............. *C07C 17/25* (2013.01); *C01B 7/0706* (2013.01); *C01B 7/0712* (2013.01); *C07C 17/087* (2013.01); *C07C 17/206* (2013.01); *C07C 17/383* (2013.01); *C07C 21/18* (2013.01)

(58) Field of Classification Search
CPC combination set(s) only.
See application file for complete search history.

(56) References Cited

U.S. PATENT DOCUMENTS 5,574,192 A    11/1996   VanDerPuy et al.
5,811,603 A     9/1998   Elsheikh
(Continued)

FOREIGN PATENT DOCUMENTS

EP    0877009 A1    11/1998
JP    H09-183740 A   7/1997
(Continued)

OTHER PUBLICATIONS

Quan et al. "Preparation of 1,1,1,3,3-pentafluropropane (HFC-245fa) by using a SbF5-attached catalyst", Journal of Fluorine Chemistry, 2007, vol. 128, pp. 190-195.
(Continued)

*Primary Examiner* — Clinton Brooks
(74) *Attorney, Agent, or Firm* — Bruce O. Bradford

(57) ABSTRACT

Disclosed is an integrated manufacturing process to co-produce (E)1-chloro-3,3,3-trifluoropropene, (E)1,3,3,3-tetrafluoropropene, and 1,1,1,3,3-pentafluoro-propane starting from a single chlorinated hydrocarbon feed stock, 240fa. The process includes a combined liquid or vapor phase reaction/purification operation which directly produces (E)1-chloro-3,3,3-trifluoropropene (1233zd(E)) from 240fa. In the second liquid phase fluorination reactor 1233zd(E) is contacted with HF in the presence of catalyst to produce 1,1,1,3,3-pentafluoropropane (245fa) with high conversion and selectivity. A third reactor is used for dehydrofluorination of 245fa to produce (E)1,3,3,3-tetrafluoropropene (1234ze(E)) by contacting in the liquid phase with a caustic solution or in the vapor phase using a dehydrofluorination catalyst. This operation may be followed by one or more purification processes to recover the 1234ze(E) product.

18 Claims, 3 Drawing Sheets

(51) Int. Cl.
  *C01B 7/07*   (2006.01)
  *C07C 17/087*  (2006.01)
  *C07C 17/20*   (2006.01)
  *C07C 17/383*  (2006.01)
  *C07C 21/18*   (2006.01)

(56) References Cited

U.S. PATENT DOCUMENTS

| | | |
|---|---|---|
| 5,895,825 A | 4/1999 | Elsheikh et al. |
| 6,362,381 B1 | 3/2002 | Wilmet et al. |
| 6,362,383 B1 | 3/2002 | Wilmet et al. |
| 6,472,573 B1 | 10/2002 | Yamamoto et al. |
| 6,844,475 B1 | 1/2005 | Tung et al. |
| 7,230,146 B2 | 6/2007 | Merkel et al. |
| 7,485,760 B2 | 2/2009 | Wang et al. |
| 7,592,494 B2 | 9/2009 | Tung et al. |
| 2005/0090698 A1 | 4/2005 | Merkel et al. |
| 2008/0051610 A1 | 2/2008 | Wang et al. |
| 2010/0072415 A1 | 3/2010 | Rao et al. |
| 2011/0172472 A1* | 7/2011 | Sakyu et al. ............... 570/160 |

FOREIGN PATENT DOCUMENTS

| | | |
|---|---|---|
| JP | H11-180908 A | 7/1999 |
| JP | 2007-509942 A | 4/2007 |
| JP | 2008-069147 A | 3/2008 |
| JP | 2010100613 A | 5/2010 |
| WO | 9724307 A1 | 7/1997 |
| WO | 9943635 A1 | 9/1999 |
| WO | 2005042451 A2 | 5/2005 |
| WO | 2009003157 A1 | 12/2008 |
| WO | WO2010035748 * | 4/2010 ............ C07C 17/20 |

OTHER PUBLICATIONS

European Search Report dated Apr. 22, 2015 from Application No. 11822463.

Japanese Office Action dated May 22, 2015 from Application No. 2013-527177.

* cited by examiner

1233zd(E), 1234ze(E), and 245fa co-production with HCl and Sulfuric Acid HF Recovery - Integrated Process Figure 2. Reaction Pressure and Temperature profiles that were observed during Experiment 3 in 1-gallon Parr reactor.

INTEGRATED PROCESS TO COPRODUCE TRANS-1-CHLORO-3,3,3-TRIFLUOROPROPENE, TRANS-1,3,3,3-TETRAFLUOROPROPENE, AND 1,1,1,3,3-PENTAFLUOROPROPANE

CROSS-REFERENCE TO RELATED APPLICATION

This application claims domestic priority from commonly owned, copending, U.S. Provisional Patent Application Ser. No. 61/379,745, filed Sep. 3, 2010, the disclosure of which is hereby incorporated herein by reference.

BACKGROUND TO THE INVENTION

The use of chlorofluorocarbons or hydrochlorofluorocarbons as foam-blowing agents has been banned due to concerns that their release damages the ozone layer. More recently, foam-blowing (addition of a volatile material to a polymeric mixture to cause a bubbled matrix which imparts insulation or cushioning value) has been accomplished through use of HFC-245fa; however, concern has been raised about the Global Warming Potential of this material.

Trans-1,3,3,3-tetrafluoropropene (HFO-1234ze(E)) and trans-1-chloro-3,3,3-trifluoropropene (HCFO-1233zd(E)), two low GWP molecules, have been identified by Honeywell as a new generation of more environmentally friendly blowing agents. Both molecules have other potential applications, such as for example, as solvents, refrigerants, aerosols, and as building blocks for making other fluorinated compounds. It is foreseeable that there will be a transition period during which all three products, i.e., HFO-1234ze(E), HCFO-1233zd(E), and HFC-245fa, will be needed. It is, therefore, desired to develop an integrated process in which all three products can be manufactured for efficiencies and synergies.

Methods for producing these three products separately are known in prior arts. U.S. Pat. No. 6,844,475, which is hereby incorporated herein as a reference, teaches a process for producing HCFO-1233zd from 1,1,1,3,3-pentachloropropane (HCC-240fa) by its reaction with hydrogen fluoride, in which the reactants are reacted in a liquid phase reaction at a temperature of less than 150° C. in the presence of a Lewis acid catalyst or mixture of Lewis acid catalysts, and hydrogen chloride and HCFO-1233zd formed in the reaction are continuously removed and the HCFO-12333zd is isolated.

The preparation of HFC-245fa from HCC-240fa is realized in a one-step process as disclosed in U.S. Pat. No. 5,574,192, or in a two-step process, as disclosed in WO 97/24307 and in U.S. Pat. No. 6,362,383. In a two-step process, HCC-240fa first reacts with hydrogen fluoride to give HCFO-1233zd, which reacts in a second step with hydrogen fluoride to give HFC-245fa.

The preparation of HCFO-1234ze(E), from HFC-245fa is taught in U.S. Pat. Nos. 7,230,146 and 7,485,760, the disclosures of which are hereby incorporated herein by reference.

The present inventors have appreciated the advantages of a flexible integrated manufacturing process in which HCFO-1234ze(E) and HFC-245fa can be co-produced from a single raw material in series and the production amount of each of the products can be easily adjusted depending on market demand.

SUMMARY OF THE INVENTION

Developing an economical process for the continuous preparation of HCFO-1233zd(E) and/or HCFO-1234ze(E) has been a goal of research in this field for some time. It has now been found that HCFO-1233zd(E), HCFO-1234ze(E), and HFC-245fa may be continuously and economically co-produced via an integrated manufacturing process. The integrated manufacturing process starts with a single chlorinated hydrocarbon, HCC-240fa.

In one embodiment of the present invention, the compounds (a) HCFO-1233zd(E), (b) HFO-1234ze(E), and (c) HFC-245fa; are co-produced in an integrated process using three reactor lines, starting with HCC-240fa.

Thus, one embodiment of the present invention is an integrated manufacturing process to coproduce HCFO-1233zd (E), HFO-1234ze(E), and HFC-245fa, starting from a single chlorinated hydrocarbon feed stock, HCC-240fa. The process includes a combined liquid or vapor phase reaction/purification operation which directly produces HCFO-1233zd(E). In the second liquid phase fluorination reactor HCFO-1233zd (E) is reacted with HF in the presence of catalyst to produce HFC-245fa, with high conversion and selectivity. Optionally, a third reactor is used for dehydrofluorination to produce HFO-1234ze(E) by contacting in the liquid phase with a caustic solution or in the vapor phase using a dehydrofluorination catalyst. This operation may be followed by one or more purification processes to recover the HFO-1234ze(E) product.

In addition to using pure HCC-240fa as the feed material, the present invention can also make use of HCC-240fa in admixture with one or more of its derivatives, such as 1,1,3,3-tetrachloropropene ($CCl_2$=$CHCHCl_2$) and/or 1,3,3,3-tetrachloropropene ($CCl_3CH$=$CHCl$), as the feed material herein. These two compounds are the dehydrochlorinated derivatives of HCC-240fa and are often present in 240fa feedstock. Accordingly, references made herein to HCC-240fa shall be understood to comprise HCC-240fa and derivatives thereof, and in particular, the derivatives 1,1,3,3-tetrachloro-propene and/or 1,3,3,3-tetrachloropropene.

This process has an economical advantage to produce HCFO-1233zd(E) over those previously known because the HCFO-1233zd(E) product is produced in a first reactor with a high selectivity, thus avoiding the need for separating HCFO-1233zd(E) and HFC-245fa products which form an azeotropic composition that makes it difficult to separate using conventional separation techniques such as distillation, thereby resulting in high product yield losses.

The disclosed process also has an advantage in that it allows for great flexibility in producing different amounts of each compound by adjusting the fractionation or distribution of the crude streams from the first and second fluorination reactors.

The disclosed integrated manufacturing process is different from prior art because it also includes the ability to recycle unreacted starting materials to maximize raw material utilization and product yields. It also discloses the ability to isolate by-products that may be sold for commercial value.

DETAILED DESCRIPTION OF THE INVENTION

Disclosed is a fully integrated co-manufacturing process for making HCFO-1233zd(E), HFC-245fa, and HFO-1234ze (E) is described below. Overall the co-production is a three step process. The chemistry involves:

Step 1:

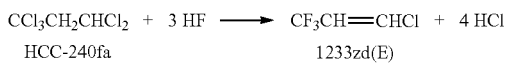

$$CCl_3CH_2CHCl_2 + 3\,HF \longrightarrow CF_3CH\!=\!CHCl + 4\,HCl$$
$$\text{HCC-240fa} \qquad\qquad\qquad \text{1233zd(E)}$$

In Step 1, the reaction of HCC-240fa with anhydrous HF in excess in a vapor phase or liquid phase reactor in such a way as to produce HCFO-1233zd(E) with a high selectivity (plus byproduct HCl). The reaction can be catalyzed or uncatalyzed.

Step 2:

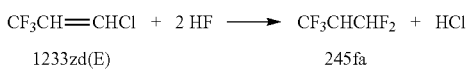

$$CF_3CH\!=\!CHCl + 2\,HF \longrightarrow CF_3CHCHF_2 + HCl$$
$$\text{1233zd(E)} \qquad\qquad\qquad \text{245fa}$$

In Step 2, a portion of the produced HCFO-1233zd(E) can be recovered as a pure component (product) and another portion can be sent to a second fluorination reactor where it is fluorinated with HF in the liquid phase in the presence of the strong fluorination catalyst such as fluorinated $SbCl_5$ catalyst to produce a second product, HFC-245fa.

Step 3:

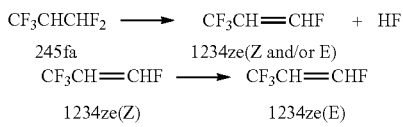

$$CF_3CHCHF_2 \longrightarrow CF_3CH\!=\!CHF + HF$$
$$\text{245fa} \qquad\qquad \text{1234ze(Z and/or E)}$$
$$CF_3CH\!=\!CHF \longrightarrow CF_3CH\!=\!CHF$$
$$\text{1234ze(Z)} \qquad\qquad \text{1234ze(E)}$$

In Step 3, a portion of HFC-245fa produced in the second fluorination reactor can be recovered as a second desired pure component (product) and another portion can be dehydrofluorinated to produce the desired third pure component (product) HCFO-1234ze(E). Also, as shown above, the Z-isomer (1234ze(Z)) can be converted to the desired trans-isomer 1234ze(E) through isomerization.

Figure 1:
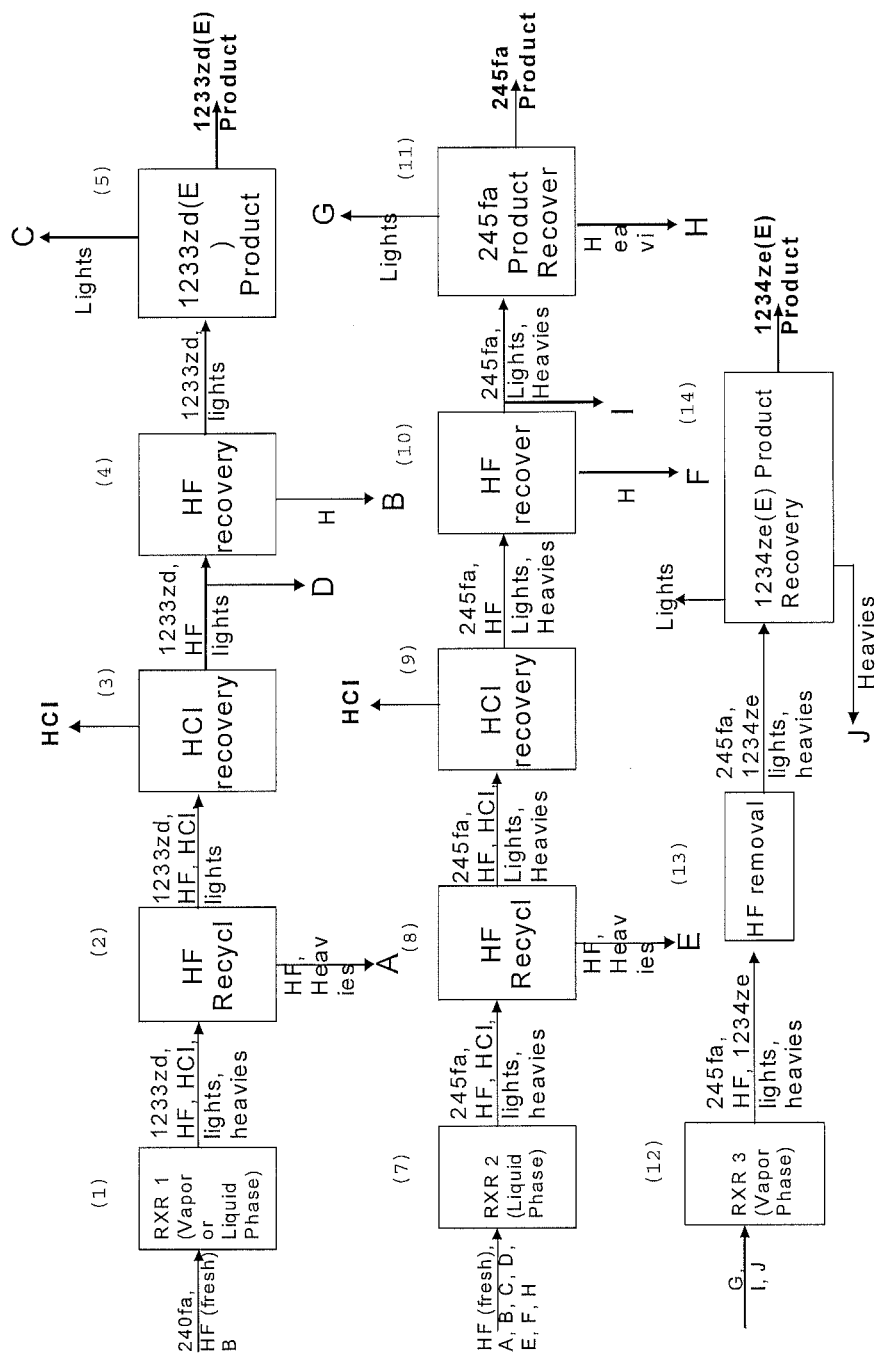
FIG. 1 shows the three integrated reactor lines used in one embodiment of the present invention.

The manufacturing process consists of the several major operations as described below. The relative positions of these process operations in the three reaction lines are shown in FIG. 1.

(1) vapor or liquid phase fluorination reaction of HCC-240fa using HF in a first reactor with simultaneous removal of byproduct HCl and the co-product 1233zd (E);
(2) separation of HF and heavy organics which are then fed to second fluorination reactor;
(3) separation and purification of byproduct HCl;
(4) separation of HF which is then fed to the second fluorination reactor,
(5) purification of first product, 1233zd(E);
(6) fluorination of 1233zd(E) with HF to produce the second co-product, 245fa, in a liquid phase catalyzed reactor;
(7) purification of the second co-product 245fa (with HCl recovery and HF recycle);
(8) dehydrofluorination of 245fa to 1234ze(E) in a third reactor (with recycle of unreacted 245fa and isomerization of 1234ze(Z) by-product); and
(9) purification of the third co-product, 1233zd(E).

These major process operations, as well as additional operations, are discussed in greater detail below.

The first fluorination reaction is conducted in a first reactor (RXR 1). This reaction can be conducted in a vapor phase in the presence of vapor phase fluorination catalyst (such as fluorinated $Cr_2O_3$) or in the liquid phase. The liquid phase reaction can be run in the absence of the catalyst or in the presence of a liquid phase fluorination catalyst such as $TiCl_4$, $FeCl_3$.

If a vapor phase reactor is utilized, then the anhydrous HF and HCC-240fa feeds are vaporized prior to entering the reactor. The product stream from the vapor phase reactor (1233zd(E), unreacted HF, and by-product HCl) are then fed to the recycle column (2). Preferably the reactor is constructed from materials which are resistant to the corrosive effects of the HF and catalyst, such as Hastelloy-C, Inconel, Monel, and Incoloy. Such vapor phase fluorination reactors are well known in the art.

For the liquid phase fluorination reaction, an agitated, temperature-controlled reactor is used for the contact of both feed materials and optionally with liquid phase fluorination catalyst. The liquid phase fluorination reactor is equipped with integrated distillation column which permits the product to leave (along with byproduct HCl, traces of light organics [principally 1234ze(E+Z)], and HF in the amount of slightly above azeotropic composition), while retaining the bulk of the HF, plus under-fluorinated organics, plus, if used, the catalyst. Preferably the reactor is constructed from materials which are resistant to the corrosive effects of the HF and catalyst, such as Hastelloy-C, Inconel, Monel, Incoloy, or fluoropolymer-lined steel vessels. Such liquid-phase fluorination reactors are well known in the art.

The starting materials, HCC-240fa and HF, are fed continuously into the first fluorination reactor. The reaction conditions (temperature, pressure, feed rates) and HF to HCC-240fa ratio are adjusted to achieve the highest selectivity to 1233zd(E) product.

The stream exiting the first reactor (RXR 1) enters a recycle column. Here the high boiling under-fluorinated or over-fluorinated intermediates and some HF are separated and are fed to the second reactor (RXR 2) for further reaction. Crude 1233zd, HF, and HCl are fed forward in the integrated process.

The stream exiting the recycle column (2) is fed to HCl recovery column. The HCl in this stream can then be purified and collected for sale using a low-temperature HCl distillation column. High purity HCl is isolated and can be absorbed in de-ionized water as concentrated HCl for sale.

The bottom stream from the HCl column (3) that contains a crude product mixture of 1233zd/lights and about 30 wt % to 50 wt % HF is fed to a sulfuric extractor or a phase separator for removal of HF from this mixture. HF is either dissolved in the sulfuric acid or phase separated from the organic mixture. HF is desorbed from the sulfuric acid/HF mixture by stripping distillation and recycled back to the reactor. The organic mixture either from the overhead of the sulfuric acid extractor may require treatment (scrubbing or adsorption) to remove traces of HF before it is fed to the 1233zd(E) product recovery train (5). Recovered HF is recycled back to first fluorination reactor (RXR 1) or is fed forward to second fluorination reactor (RXR 2).

The purification of first desired product 1233zd(E) is performed via distillation utilizing one or more of conventional distillation columns operating in a continuous mode. The purified first desired product, 1233zd(E) is collected and is available for sale. The lights and heavies are fed forward to the second fluorination reactor (RXR 2).

The reaction in RXR 2 uses a liquid phase fluorination catalyst of proper strength to achieve the desired reaction preferentially. It has been found that a catalyst comprised of antimony pentachloride (liquid under ambient conditions) which has been partially or totally fluorinated by the action of anhydrous HF achieves the desired degree of conversion without forming undesired byproducts. The catalyst fluorination is conducted by adding a specified amount of antimony pentachloride to a non-agitated, temperature-controlled reactor vessel, and adding HF by a gradual flow. A moderate amount of HCl will be generated in the operation. Conditions: 10° C. to 50° C. and at about 0 psig to 100 psig pressure. Additional fluorination catalysts that can be used include in combination with antimony pentachloride (all are partially of totally fluorinated by the action of anhydrous HF) $TiCl_4$, $TaCl_5$, $SbCl_3$.

Reaction Line 2 makes use of a reaction and stripping column. The key to this reaction is the equipment arrangement. A non-agitated, temperature-controlled reactor for the contact of both feed materials with the liquid catalyst and an integrated distillation column (operating in stripping mode) which permits the desired 245fa product to leave (along with byproduct HCl and sufficient AHF to form the azeotrope), while retaining the bulk of the HF, plus under-fluorinated and plus the catalyst is key.

Preferably the RXR 2 reactor is constructed from materials which are resistant to the corrosive effects of the HF and catalyst, such as fluoropolymer-lined steel vessels. Such liquid-phase fluorination reactors are well known in the art. Once the catalyst has been prepared, the reaction can be initiated immediately upon heating to the desired reaction temperature. The flow of HF for the catalyst preparation need not to be discontinued while the reactor is heated to a temperature of 85° C. to 115° C.

Preferably the HF feed is vaporized and superheated to provide the heat necessary to maintain proper reactor operating temperatures. Then the addition of the organic feed (1233zd) can be started immediately to cause continuous reaction while maintaining the flow of HF at an amount sufficient to produce the desired product plus an excess amount to account for losses due to azeotrope compositions of 245fa/HF that exit the top of the integrated distillation column. The reaction runs under HF rich conditions to produce the reaction product, 245fa.

Proper temperature control of the coolant and sufficient reflux action are necessary for the stripping column to be effective. General operating conditions which have been found to work well for the reaction and stripping are:
 (a) operating pressure of 80 psig to 140 psig maintained by a control valve on the exiting flow from the stripper column;
 (b) reactor temperature of 85° C. to 115° C., primarily supplied by superheating the HF vapor feed with high-pressure steam to 120° C. to 150° C. directly into the reaction mixture and steam flow into the reactor jacket;
 (c) application of brine cooling to the heat exchanger on top of the stripper column to induce reflux; temperature in the center portion of the stripper about 10° C. to 40° C. below that in the reactor;
 (d) additional heat input; and
 (e) feed rate of HF to maintain reactor and stripper conditions.

The stream exiting second reactor (RXR 2) enters a recycle column. Here the high boiling under-fluorinated or over-fluorinated intermediates and some HF are separated and are fed back to the second reactor (RXR 2) for further reaction. Crude 245fa, HF, and HCl are fed forward in the integrated process.

The stream exiting the recycle column (8) is fed to a HCl recovery column. The HCl in this stream can then be purified and collected for sale using a low-temperature HCl distillation column. High purity HCl is isolated and can be absorbed in de-ionized water as concentrated HCl for sale. Optionally water or caustic absorber can be used to remove HCl (and HF if this option is used) from the crude stream followed by a drying column.

The bottom stream from the HCl column (9) that contains a crude product mixture of 245fa/lights and about 30 wt % to 50 wt % HF is fed to a sulfuric acid extractor for removal of HF from this mixture. HF is dissolved in the sulfuric acid and separated from the organic mixture. HF is desorbed from the sulfuric acid/HF mixture by stripping distillation and recycled back to the reactor. The organic mixture either from the overhead of the sulfuric acid extractor may require treatment (scrubbing or adsorption) to remove traces of HF before it is fed to the 245fa product recovery train (11) or fed forward to the third dehydrofluorination reactor (RXR 3). Recovered HF is recycled back to second fluorination reactor (RXR 2). This HF recovery step is not necessary if an absorber (water or caustic) was used above.

Purification of the second product, 245fa, consists of two continuously operating distillation columns. The first column is used to remove light ends, mainly 1234ze(E) from the 245fa and the second column is used to remove the heavier components. The light and heavy ends that are removed from the top of the first column and bottom of the second column can both be recycled back to an earlier processing step like step (7). Optionally lights from the 245fa product recovery train, mainly 1234ze, can be fed to the dehydrofluorination reactor (RXR 3).

A portion of the stream from step (10), and the lights from the first distillation column of step (11) are fed to one or more catalyzed vapor phase reactors where the 245fa is dehydrofluorinated to produce the desired 1234ze(E) product and HF. The reactor(s) contains dehydrofluorination catalyst such as fluorinated $Cr_2O_3$ that facilitates the conversion of 245fa into 1234ze(E). The reaction conditions (temperature, pressure, feed rates) are adjusted to achieve the highest yield to 1234ze (E) product. Preferably the reactor is constructed from materials which are resistant to the corrosive effects of the HF, such as Hastelloy-C, Inconel, Monel, Incoloy. The reactor effluent is fed forward to the HF recovery system (13). Optionally, the dehydrofluorination reaction is conducted in a liquid phase using caustic as a dehydrofluorinating agent. If this option is utilized, the product stream is fed to the 1234ze (E) product recovery system (14).

The product stream exiting the dehydrofluorination reactor (RXR 3) containing mainly 1234ze(E), 1234ze(Z), and 245fa is fed to the HF removal system. The HF from the crude 1234ze(E) stream is removed using a water or caustic absorption unit followed by a drying column (13). Optionally, sulfuric acid extraction system can be used to recover HF. The acid feed crude product stream is fed forward to 1234ze(E) product recovery train (14). The step of acid recovery is not needed if caustic solution was used in dehydrofluorination step (12).

Purification of third product 1234ze(E) consists of two continuously operating distillation columns. The first column is used to remove light ends (lights) that are sent to utilization. The second column is used to remove the heavier components (heavies). The heavy ends that are removed from the bottom of the second column, mainly 1234ze(Z) and unreacted 245fa, are recycled back to the dehydrofluorination reactor (RXR 3).

The following examples are provided to further illustrate the invention and should not be taken as limitations of the invention.

EXAMPLE 1

As part of the development of a liquid phase process for making 1233zd(E) an experiment was run using no catalyst. The experiment used a 1-gallon Parr reactor and was run in a batch mode. The experiment was called Exp #3. See also, FIG. 2.

For the experiment 282.9 grams of HF and 246.2 grams of HCC-240fa (1,1,1,3,3-pentachloropropane) (12.4 to 1 mole ratio HF:240fa) were charged to the reactor at room temperature. The mixer was then turned on ensuring the reactor contents were well mixed. Then the reactor was heated to the desired temperature. Upon heating the pressure began to rise as HCl by product was produced as a result of a fluorination reaction. The reactor was heated to about 110° C. over several hours and held. The pressure was controlled in the range of 250 psig to 325 psig by venting off the HCl generated in the reaction to a dry-ice chilled dry ice trap (DIT). At the completion of the reaction after about 9.5 hrs., that was determined by lack of HCl generation, the pressure from the reactor was vented into the DIT.

The crude product from the DIT was transferred into a 1L Monel absorption cylinder (frozen in dry-ice) with about 400 grams of water. The absorption cylinder was allowed to warm up to room temperature and a sample of an organic layer that had formed in the cylinder (aqueous and organic layers were present in the cylinder upon discharge) was taken and analyzed by GC. GC results showed 4.48 GC % 245fa, 90.61 GC % 1233zd(E), 0.22 GC % 244fa, 2.93 GC % 1233zd(Z). The amount of organic collected was later quantified by further analysis of the different phases and amounted to 75.4 grams.

The organic remaining in the reactor after venting was recovered by quenching the reactor with about 300 to 400 grams of water to absorb HF and HCl, and then adding about 100 grams of carbon tetrachloride. The reactor was then opened and its contents discharged into a plastic bottle. The organic was separated from the aqueous phase by use of a reparatory funnel. The amount of heavies collected from the reactor was calculated by subtracting the weight of $CCl_4$ added to the reactor from the total weight of organic phase collected and amounted to 96.9 grams. GC/MS and GC analysis of the organic layer followed and revealed three distinct peaks attributed to under-fluorinated species HCFC-241fa, 91.057 GC %, HCFC-242fa, 0.760 GC %, and the starting material HCC-240fa, 8.183 GC %.

Experimental conditions and results of GC analysis of the reaction products are presented FIG. 2 and the tables presented below.

Figure 2:
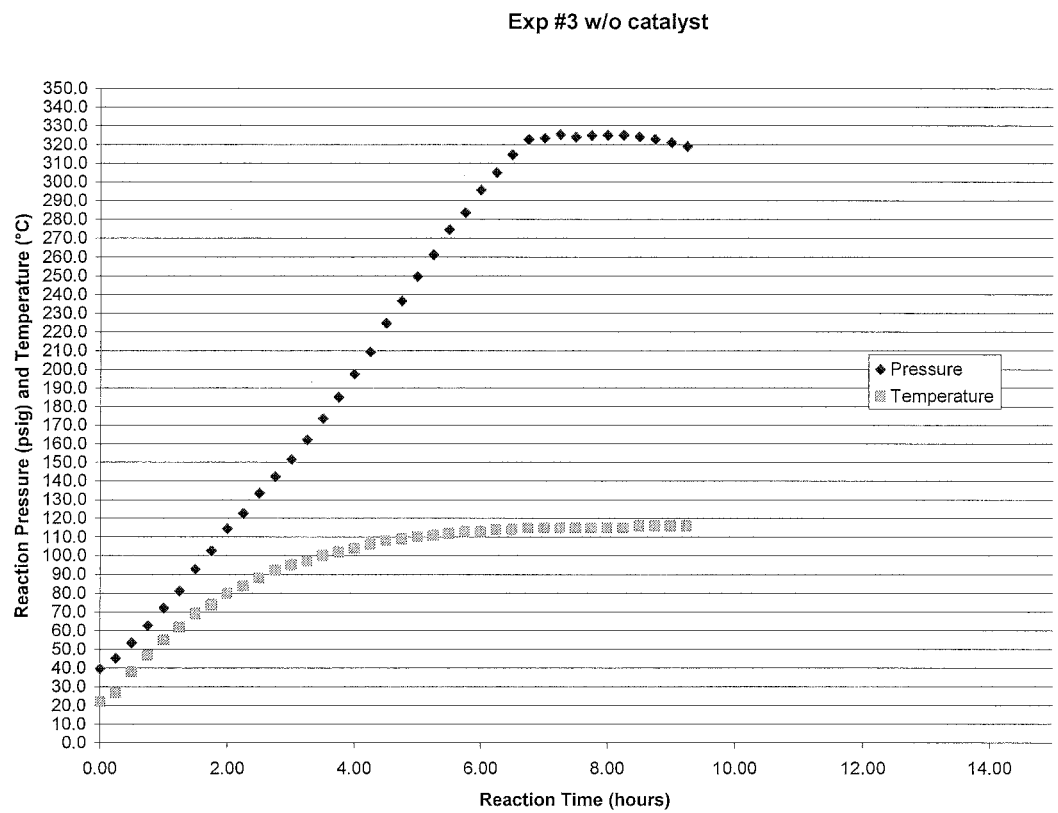
FIG. 2 illustrates reaction pressure and temperature profiles observed using Experiment No. 3—without catalyst.

FIG. 2 illustrates the Reaction Pressure and Temperature profiles that were observed during Experiment #3 in a 1-gallon Parr reactor. Reactor was charged with 282.9 grams of HF, and 246.2 grams of 240fa. Analysis of the reaction products are presented in Table I below.

TABLE I

| Exp. #3. Catalyst: No catalyst | |
| --- | --- |
| Charged to reactor | Weight (moles) |
| HF | 282.9 grams (14.145 moles) |
| 240fa | 246.2 grams (1.138 moles) |
| Collected reaction products | Weight |
| Volatile products from DIT | 75.4 grams |
| | (4.48 GC % 245fa, 90.61 GC % 1233zd(E), |
| | 0.22 GC % 244fa, 2.93 GC % 1233zd(Z)) |
| Heavies from reactor | 96.9 grams |
| | (0.760 GC % G-242, 91.057 GC % G-241, |
| | 8.183 GC % G-240fa) |

EXAMPLE 2

Dehydrofluorination of 245fa

The reaction was conducted in a two inch inner diameter Monel packed-bed reactor charged with 760 mL of fluorinated $Cr_2O_3$ catalyst. The crude product stream exiting the reactor was fed to KOH scrubber and then to a single distillation column operating in a continuous mode. The 1234ze (E) product together with light impurities was collected as a distillate from the top of the distillation column. The stream consisting mainly of unreacted 245fa and 1234ze(Z) by-product was recycled back to the reactor from the bottom of the reboiler. The reaction was conducted at catalyst bed temperature of 240° C. to 290° C. (coldest at the reactor inlet), at a reactor pressure of 5.2 psig, a constant 245fa feed rate of 1.2 lb/h, a recycle feed rate varied between 0.8 to 0.98 lb/h to maintain a constant liquid level in reboiler, and a constant overhead take-off rate of 1.02 lb/h (which is equivalent to a trans-1234ze productivity of 38 lb/ft$^3$/hr).

Figure 3:
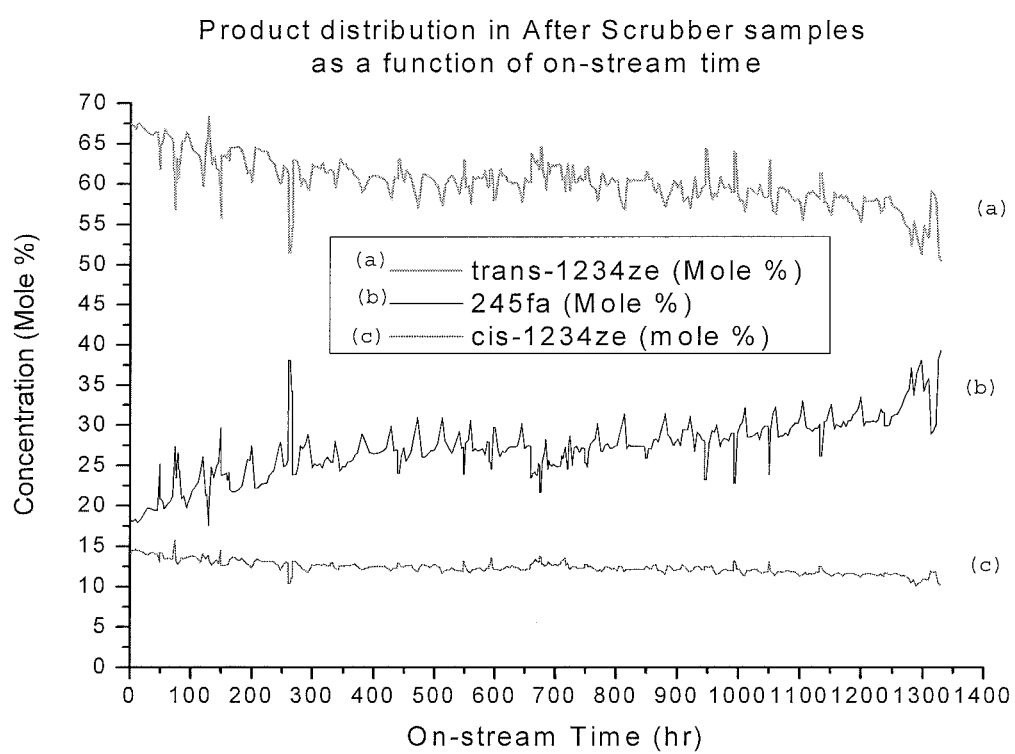
FIG. 3 illustrates the product distribution in "after scrubber" samples as a function of on-stream time. The top line is trans-HFO-1234ze (mole %); the middle line is HFC-245fa (mole %) and the bottom line is cis-HFO-1234ze (mole %).

During continuous operation, feeds and products at different sampling ports were periodically analyzed. The table below presents the results obtained at different reaction stages. The overhead product contains 40 ppm to 100 ppm 1234yf, 400 ppm to 500 ppm trifluoropropyne, 99.9+% trans-1234ze, and about 70 ppm 1234zc, indicating one distillation column is not efficient enough for product separation. Table II below gives additional information. See also, FIG. 3.

TABLE II

Compositions of recycle feed, combined feed, and products at different sampling ports

| | | Feeds | | Products | | |
| --- | --- | --- | --- | --- | --- | --- |
| Component | Time on stream H | Recycle stream Mol % | Combined stream mol % | Before scrubber mol % | After scrubber mol % | Overhead mol % |
| 1234yf | 180-200 | 0.0000 | 0.0000 | 0.0079 | 0.0073 | 0.0104 |
| 3,3,3-trifluoropropyne | | 0.0000 | 0.0000 | 0.0274 | 0.0504 | 0.0068 |
| trans-1234ze | | 0.0875 | 0.0198 | 59.9176 | 64.0869 | 99.9148 |
| 1234zc | | 0.0448 | 0.0089 | 0.0387 | 0.0312 | 0.0067 |

TABLE II-continued

Compositions of recycle feed, combined feed, and products at different sampling ports

| | | Feeds | | Products | | |
| --- | --- | --- | --- | --- | --- | --- |
| Component | Time on stream H | Recycle stream Mol % | Combined stream mol % | Before scrubber mol % | After scrubber mol % | Overhead mol % |
| 245fa | | 62.9943 | 89.7248 | 27.8974 | 22.6660 | 0.0000 |
| cis-1234ze | | 36.7607 | 10.2093 | 12.0646 | 13.1091 | 0.0000 |
| Others | | 0.1127 | 0.0372 | 0.0465 | 0.0490 | 0.0000 |
| 1234yf | 630-650 | 0.0000 | 0.0000 | 0.0026 | 0.0035 | 0.0050 |
| 3,3,3-trifluoropropyne | | 0.0000 | 0.0000 | 0.0173 | 0.0341 | 0.0468 |
| trans-1234ze | | 0.0602 | 0.0780 | 56.4184 | 60.0081 | 99.9482 |
| 1234zc | | 0.0372 | 0.0111 | 0.0341 | 0.0306 | 0.0000 |
| 245fa | | 69.0474 | 88.6978 | 32.1915 | 27.4337 | 0.0000 |
| cis-1234ze | | 30.6267 | 11.1300 | 11.2364 | 12.3887 | 0.0000 |
| Others | | 0.2285 | 0.0831 | 0.0996 | 0.1015 | 0.0000 |
| 1234yf | 1240-1280 | 0.0000 | 0.0000 | | 0.0016 | 0.0039 |
| 3,3,3-trifluoropropyne | | 0.0000 | 0.0475 | | 0.0255 | 0.0429 |
| trans-1234ze | | 0.0958 | 0.0000 | | 56.5567 | 99.9531 |
| 1234zc | | 0.0393 | 0.0184 | | 0.0278 | 0.0067 |
| 245fa | | 72.3724 | 85.9086 | | 31.8216 | 0.0000 |
| cis-1234ze | | 27.3347 | 13.9411 | | 11.4973 | 0.0000 |
| Others | | 0.1578 | 0.0844 | | 0.0695 | 0.0001 |

EXAMPLE 3

This example illustrates continuous distillation of the crude mixture consisting essentially of HCFO-1234ze(E), HCFO-1234ze(Z), and HFC-245fa that was produced in Example 2.

The distillation column consisted of a ten gallon reboiler, two inch inner diameter by ten foot column packed with propack distillation packing and a shell and tube condenser. The column had about 30 theoretical plates. The distillation column was equipped with reboiler level indicator; temperature, pressure, and differential pressure transmitters. The distillation was run at pressure of about 50 psig and differential pressure of about 17 inches of $H_2O$ in the continuous mode.

The feed consisting essentially of HCFO-1234ze(E), HCFO-1234ze(Z), HFC-245fa, and small amount of impurities (see Table III below) was continuously fed via the inlet port at the bottom of the distillation column at the rate of about 1.75 lb/hr. The distillate consisting essentially of HCFO-1234ze(E) and light impurity (see Table III) was collected from the top of the condenser at the rate of about 1.02 lb/hr. The stream consisting essentially of HFC-245fa and HCFO-1234ze(Z) (see Table III below) was continuously taken out from the bottom of reboiler at the rate of about 0.73 lb/hr in order to maintain the level of material in the reboiler at about 40%. The distillation was run continuously for about 1000 hours.

EXAMPLE 4

This example illustrates the semi-batch reaction where HF was continuously fed into a charge of titanium tetrachloride catalyst and 1,1,1,3,3-pentachloropropane (HCC-240fa).

A clean, empty ten gallon jacketed, agitated reactor of Hastelloy C construction was prepared. This reactor was connected to a two inch inner diameter vertical, PTFE-lined pipe containing packing material (stripper), which was in turn connected to an overhead heat exchanger. The heat exchanger was supplied with −40° C. brine circulation on the shell side. Vapors exiting this stripper were processed through a scrubber, in which temperature-controlled dilute potassium hydroxide aqueous solution was circulated. Vapors exiting this stripper were collected in a weighed, chilled (−40° C.) cylinder referred to as the product collection cylinder, followed by a smaller cylinder in series chilled in a dry ice bath.

For this example, 14 lbs. of anhydrous HF was fed to assure catalyst fluorination. Next, 1.5 lbs. of $TiCl_4$ was added as a catalyst. HCl was immediately generated as observed by the build-up of pressure in the reactor. After the pressure was reduced by venting most of the HCl from the system, 50 lbs. of HCC-240fa was added. The reactor was heated. At about 85° C. HCl started to be generated indicating that the fluorination reaction was initiated. The system pressure was controlled at about 120 psig. Additional HF was then fed con-

TABLE III

Composition of 1234ze(E) distillation column streams

| | 3,3,3-trifluoropropyne Wt. % | HCFO-1234ze(E) Wt. % | HCFO-1234zc Wt. % | HCFO-1234ze(Z) Wt. % | HCFO-1233zd Wt. % | HFC-245fa Wt. % |
| --- | --- | --- | --- | --- | --- | --- |
| Feed composition | 0.0263 | 58.1003 | 0.0253 | 11.3939 | trace | 30.4542 |
| Distillate composition | 0.0497 | 99.9503 | 0.0000 | — | — | — |
| Bottoms composition | — | 0.0801 | 0.0604 | 27.1886 | trace | 72.6709 | tinuously and product was collected in the product collection cylinder until the HCC-240fa was consumed.

The GC analysis of the crude material collected during the run was as follows; 86.4% 1233zd(E); 5.5% G-244fa; 3.1% 1234ze(E); 1.5% 1233zd(Z); 1.1% 1234ze(Z); 1.1% dimer; 0.2% trifluoropropyne.

EXAMPLE 5

This example illustrates the recovery of anhydrous HF from a mixture of HF, HCFO-1233zd, and HCFC244fa according to certain preferred embodiments of the present invention.

A mixture consisting of about 70 wt. % HCFO-1233zd(E) and about 30 wt. % HF is vaporized and fed to the bottom of a packed column at a feed rate of about 2.9 lbs per hour for about 4 hours. A stream of about 80 wt. % sulfuric acid (80/20 $H_2SO_4/H_2O$) with about 2% HF dissolved therein is fed continuously to the top of the same packed column at a feed rate of about 5.6 lbs per hour during the same time frame. A gaseous stream exiting the top of the column comprises HCFO-1233zd(E) with less than 1.0 wt. % HF therein. The concentration of HF in the sulfuric acid in the column bottoms increases from 2.0 wt. % to about 15 wt. %.

The column bottoms containing sulfuric acid and about 15 wt. % HF is collected and charged into a two gallon Teflon® lined vessel. The mixture is heated to about 140° C. to vaporize and flash off HF product, which is collected. The collected HF product contains about 6000 ppm water and 500 ppm sulfur. The sulfuric acid contains about 500 ppm of TOC (total organic carbon).

The HF collected from flash distillation is distilled in a distillation column and anhydrous HF is recovered. The recovered anhydrous HF contains less than 50 ppm of sulfur impurities and lees than 100 ppm water

EXAMPLE 6

This example demonstrates the purification of the acid free 1233zd(E) crude product.

92 lbs of acid free 1233zd crude material produced in Example 1 was charged to a batch distillation column. The crude material contained about 94 GC area % and 6 GC area % impurities. The distillation column consisted of a 10 gallon reboiler, two inch inner diameter by 10 feet propack column, and a shell and tube condenser. The column had about 30 theoretical plates. The distillation column was equipped with temperature, pressure, and differential pressure transmitters. About 7 lbs of a lights cut was recovered which consisted of mainly 1234ze(Z+E), trifluoropropyne, 245fa, and 1233zd (E). 82 lbs of 99.8+GC area % 1233zd(E) were collected. The reboiler residue amounting to about 3 lbs was mainly 244fa, 1233zd(Z), 1233zd dimmer, and 1233zd(E). The recovery of 99.8+GC area % pure 1233zd(E) was 94.8%.

EXAMPLE 7

In this example, a continuous liquid phase fluorination of a mixed stream containing 1233zd(Z) and 1233zd(E) is demonstrated. The fluorination catalyst for the example is $SbCl_5$.

6500 grams of $SbCl_5$ are contained in a Teflon®-lined liquid phase reactor equipped with a catalyst stripper, two inch inside diameter packed column and with a condenser whose function is to return entrained catalyst, some of the unreacted HF and some of the unreacted organic back to the reactor when the system is running in continuous reaction mode. The reactor is 2.75-inch inside diameter×36-inch long and is not equipped with a mixer/agitator. The reactor is heated to between about 85° C. to 87° C. The catalyst is then activated by the addition of 1500 grams of HF followed by 1500 grams of $Cl_2$. HCl generated by the fluorination of the catalyst raises the reaction system pressure to about 100 psig where it is controlled.

The continuous gaseous HF feed is started first. It is bubbled into the liquid catalyst through a dip tube at a rate of 1.9 lb/hr, and when 1.0 lb of HF has been added, the mixed organic feed stream is introduced. It also enters the liquid catalyst by way of a dip tube and consist of about 95% 1233zd(E) and 5% 1233zd(Z). The mixed organic is fed continuously at rate of 2.0 lb/hr. The mole ratio of HF to organic raw material is 7:1. The reaction temperature is maintained at 90° C. to 95° C. and the pressure is maintained at 120 psig. 245fa, unreacted organic, organic by-products, HCl, and unreacted HF exit the top of the catstripper column. The experiment is run continuously for over 500 hours and the average conversion of the organic raw material is greater than 99.5% while the selectivity to 245fa reaches 99.5%. $Cl_2$ (0.02 mole/mole organic) is continuously fed into the reaction mixture on a periodic basis through a dip tube in order to keep the catalyst active.

EXAMPLE 8

245fa crude material exiting a fifty gallon pilot plant fluorination reaction system was contacted with water in an absorption column to remove HCl and HF. Only a trace amount of acid remained. This stream was then contacted by a dilute caustic stream in a second absorber removing the remaining acid. The stream was then passed through a column containing X13 molecular sieves to remove any moisture that was added to the stream during contact with water during the acid removal step.

EXAMPLE 9

The dried and acid free 245fa crude material from Example 8 was then distilled continuously to greater than 99.95% purity using a series of two conventional distillation columns to remove most of the low and high boiling impurities.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. A process to co-produce three products, (E)1-chloro-3, 3,3-trifluoropropene (1233zd(E)), (E)1,3,3,3-tetrafluoropropene (1234ze(E)), and 1,1,1,3,3-pentafluoro-propane (245fa) starting from 1,1,1-3,3-pentachloropropane (HCC-240fa) comprising the steps of:
(a) in a first reactor, conducting the fluorination of HCC-240fa with HF and a fluorinated $TiCl_4$ catalyst to produce a yield of about 85% (E)1-chloro-3,3,3-trifluoropropene (1233zd(E)) and isolating a portion of the 1233zd(E) product;
(b) in a second reactor, conducting the fluorination of a portion of the 1233zd(E) formed in step (a) to produce 1,1,1,3,3-pentafluoropropane (245fa) and isolating a portion of the 245fa product; and
(c) in a third reactor, conducting the dehydrofluorination of a portion of the 245fa formed in step (b) to produce (E)1,3,3,3-tetrafluoropropene (1234ze(E)) and isolating a portion of the 1234ze(E) product;
wherein the HCFO-1233zd(E) product is produced in the first reactor with high selectivity, thereby avoiding the formation of an azeotropic composition consisting of HCFO-1233zd(E) and HFC-245fa;
wherein the process includes the recycling of unreacted starting materials to maximize raw material utilization and product yields;
wherein the process further includes the isolation of by-products of the reactions; and
wherein by adjusting the distribution of the crude streams from the first and second fluorination reactors, different amounts of each product are generated during the process.

2. The process of claim 1, wherein the dehydrofluorination catalyst is fluorinated $Cr_2O_3$.

3. The process of claim 1, further comprising one or more purification steps to recover the 1233zd(E), 245fa, and 1234ze(E) products.

4. The process of claim 1, wherein the fluorination of HCC-240fa is conducted using HF and $TiCl_4$ in a first reactor to produce a yield of about 90% of 1233zd(E).

5. The process of claim 1, wherein the step (a) fluorination process is a liquid phase reaction.

6. The process of claim 1, wherein the step (b) fluorination process is a liquid phase catalyzed reaction.

7. The process of claim 1, wherein the step (a) fluorination process further includes removal of byproduct HCl.

8. The process of claim 1, wherein step (c) further includes isomerization of 1234ze(Z) by-product.

9. The process of claim 1, wherein the HCC-240fa further includes 1,1,3,3-tetrachloro-propene, 1,3,3,3-tetrachloropropene, or a mixture thereof.

10. A process to co-produce (E)1-chloro-3,3,3-trifluoropropene (1233zd(E)), (E)1,3,3,3-tetrafluoropropene (1234ze(E)), and 1,1,1,3,3-pentafluoro-propane (245fa) starting from 1,1,1-3,3-pentachloropropane (HCC-240fa) comprising the steps of:
(a) in a first reactor, conducting the fluorination of HCC-240fa with $TiCl_4$ catalyst to produce a yield of about 85% (E)1-chloro-3,3,3-trifluoropropene (1233zd(E));
(b) in a second reactor, conducting the fluorination of a portion of the 1233zd(E) with $SbCl_5$ catalyst to produce a yield of about 90% 1,1,1,3,3-pentafluoropropane (245fa); and
(c) in a third reactor, conducting the dehydrofluorination of a portion of the 245fa with fluorinated $Cr_2O_3$ and KOH to produce a yield of about 90% (E)1,3,3,3-tetrafluoropropene (1234ze(E));
wherein the HCFO-1233zd(E) product is produced in the first reactor with high selectivity, thereby avoiding the formation of an azeotropic composition consisting of HCFO-1233zd(E) and HFC-245fa;
wherein the process includes the recycling of unreacted starting materials to maximize raw material utilization and product yields;
wherein the process further includes the isolation of by-products of the reactions; and
wherein by adjusting the distribution of the crude streams from the first and second fluorination reactors, different amounts of each product are generated during the process.

11. The process of claim 10, wherein the dehydrofluorination catalyst is fluorinated $Cr_2O_3$.

12. The process of claim 10, further comprising one or more purification steps to recover the 1233zd(E), 245fa, and 1234ze(E) products.

13. The process of claim 10, wherein the fluorination of HCC-240fa is conducted using HF and $TiCl_4$ in a first reactor to produce a yield of about 90% of 1233zd(E).

14. The process of claim 10, wherein the step (a) fluorination process is a liquid phase reaction.

15. The process of claim 10, wherein the step (b) fluorination process is a liquid phase catalyzed reaction.

16. The process of claim 10, wherein the step (a) fluorination process further includes removal of byproduct HCl.

17. The process of claim 10, wherein step (c) further includes isomerization of 1234ze(Z) by-product.

18. The process of claim 10, wherein the HCC-240fa further includes 1,1,3,3-tetrachloro-propene, 1,3,3,3-tetrachloropropene, or a mixture thereof.

* * * * *